United States Patent
Mazzucchelli

(10) Patent No.: US 9,504,598 B2
(45) Date of Patent: Nov. 29, 2016

(54) ADAPTABLE PROTECTIVE DEVICE

(71) Applicant: Alessandro Mazzucchelli, Sale Marasino (IT)

(72) Inventor: Alessandro Mazzucchelli, Sale Marasino (IT)

(73) Assignee: ADVANCE KITES S.R.L., Sale Marasino (IT)

( * ) Notice: Subject to any disclaimer, the term of this patent is extended or adjusted under 35 U.S.C. 154(b) by 91 days.

(21) Appl. No.: 14/327,993

(22) Filed: Jul. 10, 2014

(65) Prior Publication Data

US 2016/0008159 A1 Jan. 14, 2016

(51) Int. Cl.
*A61F 5/00* (2006.01)
*A61B 19/00* (2006.01)
*A61F 5/058* (2006.01)

(52) U.S. Cl.
CPC ........... *A61F 5/05816* (2013.01); *A61F 5/058* (2013.01)

(58) Field of Classification Search
USPC ...................... 128/869, DIG. 20; 602/6–8, 13
See application file for complete search history.

(56) References Cited

U.S. PATENT DOCUMENTS

| | | | | |
|---|---|---|---|---|
| 3,212,497 A * | 10/1965 | Dickinson | ............ | A61B 6/0421 128/DIG. 20 |
| 3,745,998 A * | 7/1973 | Rose | ....................... | A61F 5/055 128/DIG. 15 |
| 3,762,404 A * | 10/1973 | Sakita | ................... | A43B 17/035 128/DIG. 20 |
| 4,657,003 A * | 4/1987 | Wirtz | .................. | A61F 5/05833 128/869 |
| 5,009,318 A * | 4/1991 | Lepinoy | ............. | A61G 7/05753 128/DIG. 20 |
| 5,954,676 A * | 9/1999 | Kramer, III | ......... | A61F 5/05816 128/DIG. 20 |
| 7,094,212 B2 * | 8/2006 | Karason | ................... | A61F 13/04 602/13 |
| 7,309,321 B2 * | 12/2007 | Farley | ..................... | A61F 5/055 602/18 |
| 8,082,924 B2 * | 12/2011 | Fischer | .................... | A61B 6/04 128/869 |
| 2003/0139695 A1 * | 7/2003 | Riach | ..................... | A61F 5/012 602/13 |

FOREIGN PATENT DOCUMENTS

| | | |
|---|---|---|
| EP | 1 985 265 A1 | 10/2008 |
| WO | 98/46174 A1 | 10/1998 |
| WO | 2012/093992 A1 | 7/2012 |

OTHER PUBLICATIONS

Italian Search Report for Italian Application No. MI20131098, 2 pages, completed on Mar. 17, 2014.

\* cited by examiner

*Primary Examiner* — Kim M Lewis

(74) *Attorney, Agent, or Firm* — Vorys, Sater, Seymour & Pease LLP

(57) ABSTRACT

Provided is an adaptable protective device configured to include a portion of body to protect, including: a main casing impermeable to the passage of fluid, flexible and defining a main volume, the main casing being configured to be placed at least partially around the portion of body to protect so that the portion of body to protect is outside the main volume, the main casing defining an inner surface substantially in contact with the portion of body to protect and an outer surface not in contact with the portion of body to protect, an inner casing placed inside the main casing, permeable to the passage of fluid and flexible; and including a plurality of filler particles, a first valve, configured to form or interrupt a connection for fluid passage between the main volume and the external environment, a closure casing impermeable to the passage of fluid, flexible and including sealing means configured to create a fluid seal between the closure casing and the portion of body to protect thereby forming a closed volume impermeable to the passage of fluid and including the main casing and the portion of body to protect.

10 Claims, 4 Drawing Sheets

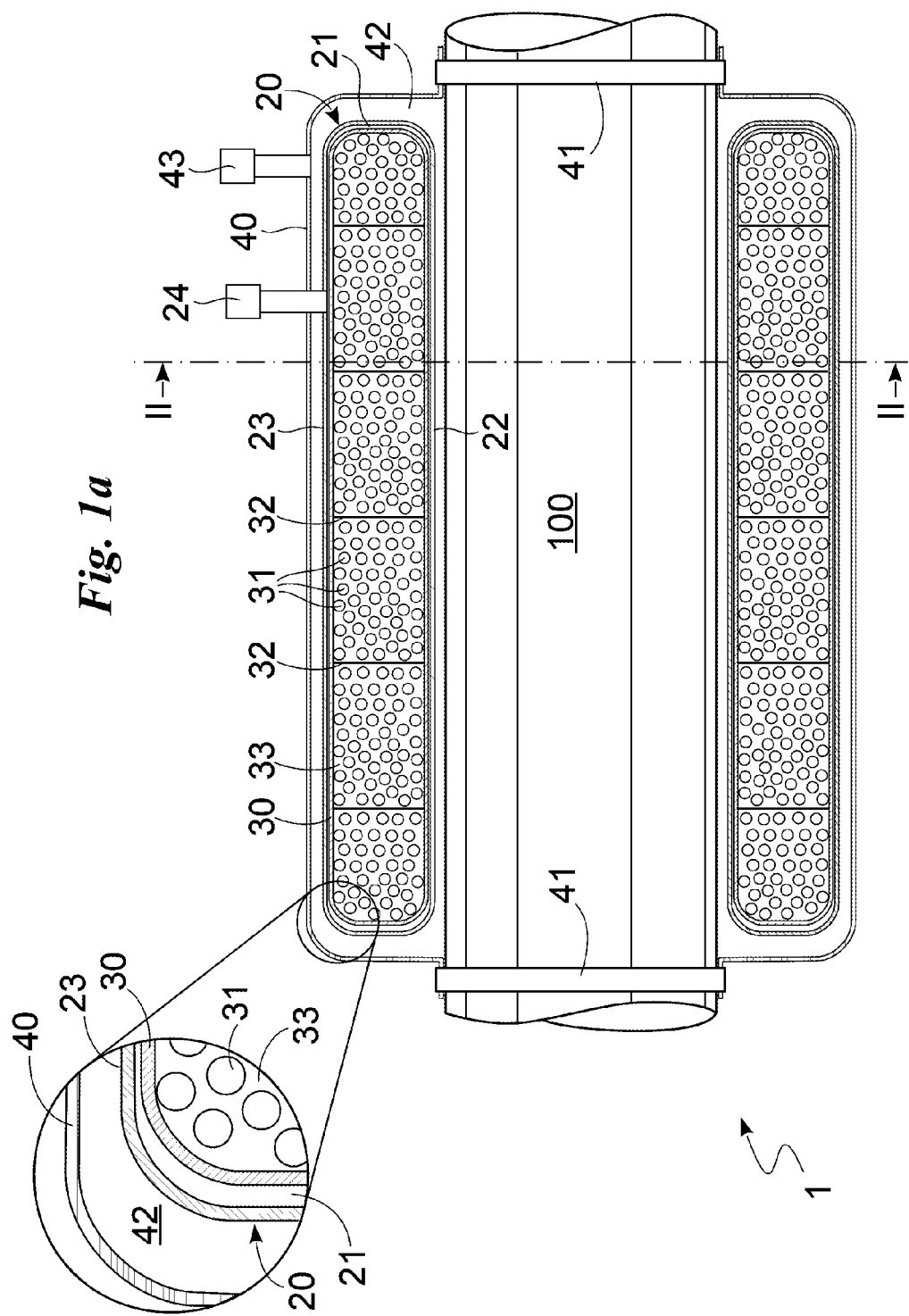

ADAPTABLE PROTECTIVE DEVICE

TECHNICAL FIELD OF THE INVENTION

Subject of the present invention is an adaptable protective device suitable to include a portion of body to protect comprising a main casing impermeable to the passage of fluid, flexible and defining a main volume, the main casing being suitable to be placed at least partially around the portion of body to protect so that the portion of body to protect is outside the main volume, the main casing defining an inner surface substantially in contact with the portion of body to protect and an outer surface not in contact with the portion of body to protect, an inner casing placed inside the main casing, permeable to the passage of fluid and flexible; a plurality of filler particles housed in the inner casing; a first valve suitable to form or interrupt a connection for fluid passage between the main volume and the external environment and suitable to permit the depressurisation of the main volume defining a relaxed configuration in which the filler particles are movable inside the at least one inner casing; and a compressed configuration in which the filler particles are compacted and substantially define at least one solid body.

In particular, the invention concerns a particular device suitable to protect and immobilize a portion of the human body or an object.

DESCRIPTION OF THE PRIOR ART

Various types of protective devices are presently known, as plasters and rigid bandages for persons for healing purposes, rigid boots for persons for sport activities, casings for fragile items and the like, and more.

For example various devices exist made of deformable and hardening materials, such as polymers, hardening foams and more. Such materials can adapt to the shape of the item to protect when in a deformable state, and then they stiffen and protect the item contained within.

The protection conferred by these is particularly due to the fact, that such devices distribute any external shocks in an uniform way on the entire element they protect.

Other protective devices are rigid bandages for orthopedic injuries, as well as so called plasters, Tensoplast and similar. Such devices also make use of a deformable item, which is then hardened by a triggered chemical reaction.

The item being deformable, it is possible to adapt the same to the shape of the portion of the body to bandage or immobilize.

Such devices have the drawback of not perfectly protecting and not permitting a reuse, being disposable.

An important development has been carried out by the same Applicant. Such innovation is described in Patents WO-A-2012/114300 and WO-A-2012/114301, in which items are described including inner volumes containing rigid particles. From such volumes air can also be extracted, so that due to the depression the rigid particles become compact by making a rigid counter-shaped body with respect to the shape of the item on which they have been placed.

Similar devices, even for different purposes, are described in Patent WO-A-2012/114301.

However, the first of such documents describes a protective item capable of only partially wrapping the item it protects. Such solution is optimal in many, but not in all cases. For example, such solution is not optimal for immobilizing limbs and similar, for which it is important to completely wrap the entire limb at 360° and not only a portion of the same. In fact, if one of such devices is wrapped around a cylindrical item with a broadly-angled circumferential sector, for example greater than the flat angle, during the air suction each portion of the protective device contracts approaching its own centre, so moving away from the item to protect and not completely performing the protection.

Furthermore, the second of such documents describes a device which permits to completely protect only items comprised and contained within a casing. The same solution is therefore not applicable to human limbs, portions of elongated items or of great dimension and other more. In this situation the technical task of the present invention is to conceive an adaptable protective device suitable to substantially obviate the cited drawbacks.

SUMMARY OF THE INVENTION

Within said technical task an important aim of the invention is to provide an adaptable protective device which precisely adapts to the portion of an item around which it wraps, even if it is wrapped for broad angles.

Another important aim of the invention is to conceive a protective device usable several times.

The technical task and the specified aims are reached by an adaptable protective device suitable to include a portion of body to protect comprising a main casing impermeable to the passage of fluid, flexible and defining a main volume, the main casing being suitable to be placed at least partially around the portion of body to protect so that the portion of body to protect is outside the main volume, the main casing defining an inner surface substantially in contact with the portion of body to protect and an outer surface not in contact with the portion of body to protect, an inner casing placed inside the main casing, permeable to the passage of fluid and flexible; a plurality of filler particles housed in the inner casing; a first valve suitable to form or interrupt a connection for fluid passage between the main volume and the external environment and suitable to permit the depressurisation of the main volume defining a relaxed configuration in which the filler particles are movable inside the at least one inner casing; and a compressed configuration in which the filler particles are compacted and substantially define at least one solid body, a closure casing impermeable to the passage of fluid, flexible and comprising sealing means suitable to create a fluid seal between the closure casing and the portion of body to protect thereby forming a closed volume impermeable to the passage of fluid and including the main casing and the portion of body to protect, a second valve suitable to form or interrupt a connection for fluid passage between the closure volume and the external environment and suitable to permit the depressurisation of the closure volume defining a closed configuration in which the closure casing is depressurised and the atmospheric pressure presses, in all directions, the inner casing against the portion of body to protect.

BRIEF DESCRIPTION OF THE DRAWINGS

The features and advantages of the invention are explained in the following by the detailed description of a preferred embodiment of the invention, with reference to the annexed drawings, in which:

FIG. 1a shows a sagittal section of an adaptable protective device according to the invention in a first configuration;

FIG. 2 is the cross section showing a portion of the adaptable protective device according to the invention, in the configuration of FIG. 1a;

DESCRIPTION OF PREFERRED EMBODIMENTS

Figure 1B:
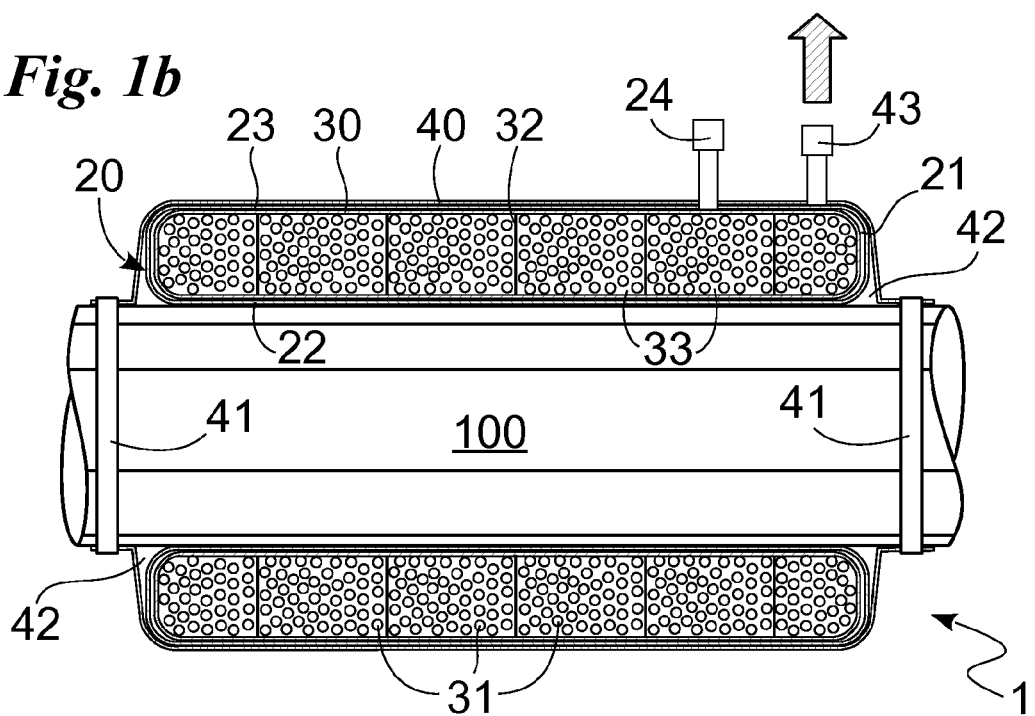
FIG. 1b shows a sagittal section of the adaptable protective device according to the invention in a second configuration.

With reference to cited Figures the adaptable protective device according to the invention is indicated as a whole with 1.

It is suitable to include a portion of the body to protect 100, in particular a portion of a human body, such as a limb, a foot or hand for medical purposes or as a simple support (shoes, various protections) or a portion of a body made of a device which is not a portion of a human and/or animal body, for example of a mechanical or electronic item of any other type and shape. The same device 1 is suitable in all those cases in which the same cannot be entirely contained within a closure casing. The device 1 can then be either a protection of a portion of a human or animal body, or a protection of an object.

The device 1 comprises a main casing 20 impermeable to the passage of fluid, flexible and defining a main volume 21. It is for example made of a polymeric and elastic membrane, so that the protective device 1 adapts to the shape of the portion of the body with which the same device 1 is associated. In detail, it is preferably made either of a EVA foam with closed cells, polychloroprene or Neoprene®, polyvinylchloride or of composite materials and more.

The main casing 20 is suitable to be placed at least partially around said portion of body to protect 100, so that said portion of body to protect 100 is at the outside of said main volume 21. The main casing 20 also defines an inner surface 22 substantially in contact with said portion of body to protect 100 and an outer surface 23 not in contact with said portion of body to protect 100.

The device 1 also comprises an inner casing 30 placed at the inside of the main casing 20 and permeable to the passage of fluid, and flexible. The inner casing 30 in turn includes a plurality of filler particles 31. The inner casing 30 preferably has a plurality of intermediate casings 33 mutually separated through walls 32 permeable to the passage of fluid and flexible and preferably made of the same material of the inner casing 30. The inner casing 30 and the walls 32 are preferably completely permeable to fluids, then they are made of permeable materials due to their intrinsic and microscopic features, such as for instance textiles. In particular, they are suitably elastic so to permit, as better described in the following, to define the relaxed and compressed configuration. More in particular, they are elastic textiles such as Lycra® or similar.

The intermediate casings 33 permit to uniformly place the filler particles 31 and avoid that the same accumulate just in a few portions of the inner casing 30. The walls 32 then permit to obtain intermediate casings 33 having selected sizes in the three dimensions, in particular according to the height given by the height of the single walls 32.

The particles 31 can have various shapes, materials and dimensions and be of different types in order to define a particular physical feature of the assembly of particles in a compressed configuration.

In particular one type of particles can be characterized by particles 31 made of the same material and having for example dimensions and shapes also variable from one particle to the other.

Another type of particles 31 can be characterized by particles 31 all having the same shape and dimension, and possibly also made of partially different materials but having similar mechanical characteristics.

A further type can also be made of very homogeneous particles 31 all having certain sizes, shapes and materials, and mutual variations comprised within strict tolerances.

The main casing 20 then comprises a first valve 24 suitable to realize or interrupt a connection for fluid passage, preferably gas and better air, between the main volume 21 and the external environment and suitable to permit the depressurization of said main volume 21, and consequently also of the inner casing 30 and of the various intermediate casings 33, so defining a relaxed configuration (FIG. 1a, FIG. 1b), in which the filler particles 31 are movable inside said inner casing 30; and a compressed configuration (FIG. 1d) in which said filler particles 31 are compacted and substantially define at least one solid body 31a.

Thanks to said partition of the types of particles, it is possible to obtain solid bodies 31a with different physical and mechanical features according to the type of particles 31. For example in a medical plaster it is possible to place smaller or more elastic particles 31, which make softer and/or more elastic bodies 31a, at the skin or less resistant body parts like fingers, and more rigid or bigger particles 31, which make stiffer and more resistant bodies 31a, at a distance from the skin or at body portions like elbows or similar. The same argument applies to objects having stiff and fragile portions.

The device 1 also comprises a closure casing 40 impermeable to the passage of fluid and flexible and preferably elastic. It can be made of a polymeric membrane, like those for making bags or more.

The closure casing 40 comprises sealing means 41 suitable to create a fluid seal between said closure casing 40 and said portion of body to protect 100, consequently making a closure volume 42, impermeable to the passage of fluid, and including said main casing 20 and said portion of body to protect 100.

The sealing means 41 can be simple elastic bands, one or two and more depending on the shape of the body and of the portion of body to protect 100. They close the closure casing 40 on the body to protect 100.

The casing 40 also comprises a second valve 43 suitable to realize or interrupt a fluid passage connection, preferably gas and better air, between the closed volume 42 and the external environment and suitable to permit to depressurize said closed volume 42 by defining a closure configuration (FIG. 1c, FIG. 1d) in which the closure casing 40 is depressurized and the atmospheric pressure pushes, in any direction, the inner casing 41 against the portion of body to protect 100. The first valve 24 also comprises connection means with the closure casing 40 suitable to permit the passage of the same through the casing 40 and one of its controls from outside. For example, a particular free solvable connection is possible between the valve and the casing 40 and another valve connected with the casing 40 or other more.

The valves 24 and 43 are finally preferably one-way-valves suitable to permit the inlet and not the outlet of air from the casings 40 and 20, unless a different control, similar to that of the inner tubes for tires but operating in an opposite direction.

The adaptable protective device 1 also comprises a heat exchange channel 50, partially disposed inside said main casing 20 and in particular interposed between the inner casing 30 and the main casing 20 at the inner surface. It is preferably flexible and made of a polymeric material and is suitable to regulate the temperature of the portion of body to protect 100, thanks to the possibility of flowing a fluid, in particular a liquid, to the inside of the same, at the desired temperatures. The heat exchange channel 50 suitably follows a serpentine path.

The invention also comprises a new method of protection of a portion of a body to protect 100, preferably done with the adaptable protective device 1 described before and coincident with the method of utilization of the same device.

Such method comprises the step of placing the main casing 20, including the inner casing 30 with the various intermediate casings 33 and particles 31, around the portion of body to protect 100.

The closure casing 40 is then placed around the outer surface 23 of the main casing 20, and sealing means 41 are placed suitable to make a fluid sealing between the closure casing 40 and the portion of body 41. The sealing means 41 and the closure casing 40 consequently make the closed volume 42 impermeable to the fluid passage and including the main casing 20, in turn including the inner casing 30 with the various intermediate casings 33 and particles 31, and the portion of body to protect 100. Such configuration is illustrated in FIG. 1a. Furthermore in such configuration the particles 31 are free to move within the intermediate casings 33 and so the inner casing 30 and consequently the inner casing 30 and the main casing 20 and the closure casing 40 are freely adaptable to the shape of the portion of body to protect 100.

Subsequently, as shown in FIG. 1b, the closure volume 42 is depressurized through the first valve 24, by defining a closure configuration in which the closure casing 40 is pushed by the atmospheric pressure and in turn it pushes in any direction, against the main casing 20 and against the inner casing 30 and the particles 31 and consequently pushes the device 1 against the portion of body to protect 100.

Figure 1C:
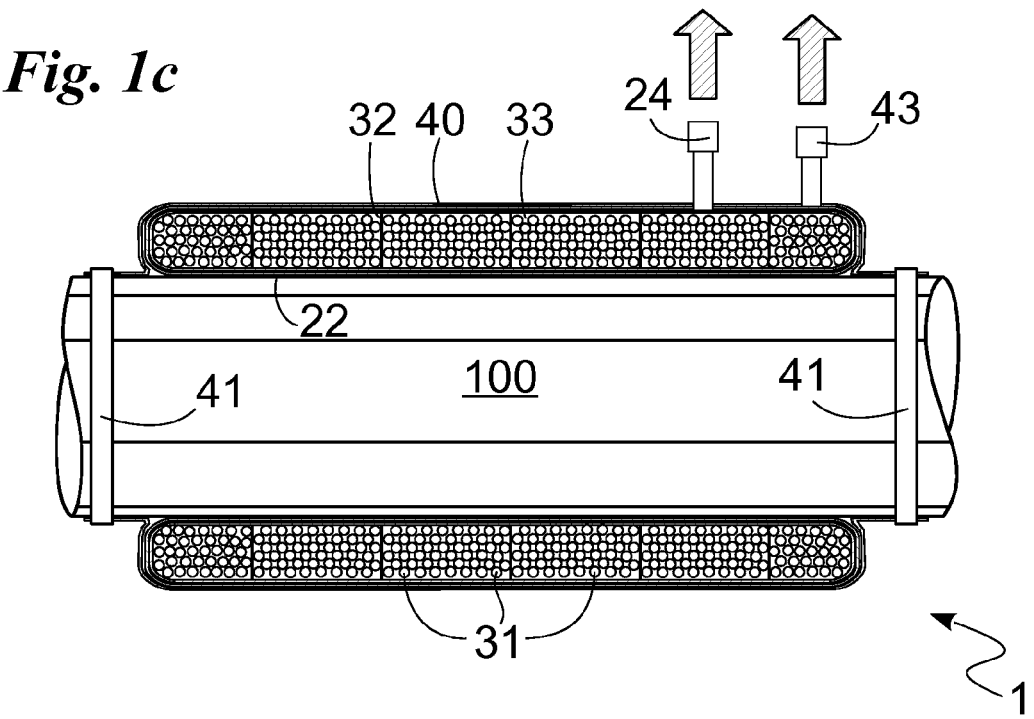
FIG. 1c shows a sagittal section of the adaptable protective device according to the invention in a third configuration.

Still subsequently, or at the same time with the preceding step, the main volume 21 is depressurized through the second valve 43, as illustrated in FIG. 1c, by defining a compressed configuration in which the filler particles 31 are compacted and substantially define at least one solid body 31a, perfectly profiled regarding the shape of the portion of body to protect 100.

Figure 1D:
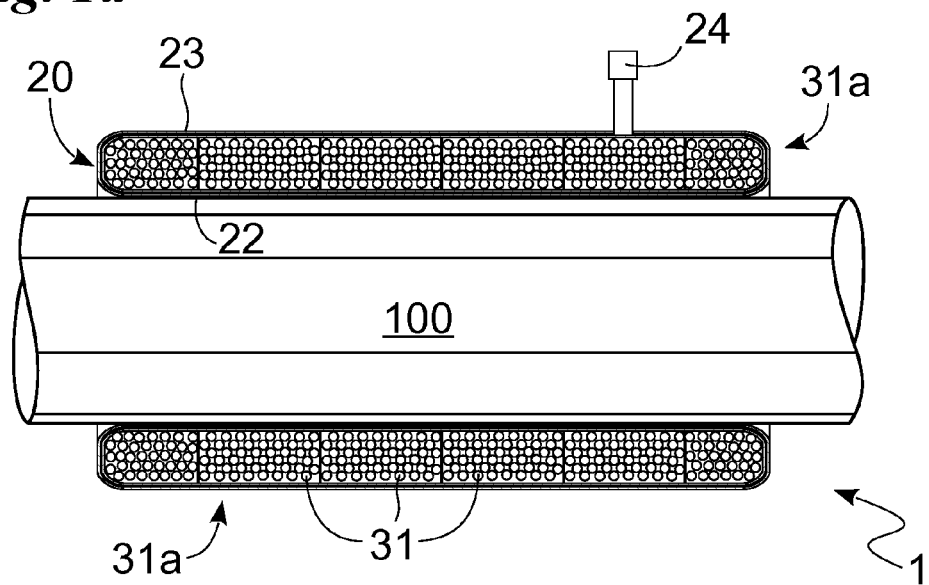
FIG. 1d shows a sagittal section of the adaptable protective device according to the invention in a fourth configuration.
Figure 3:
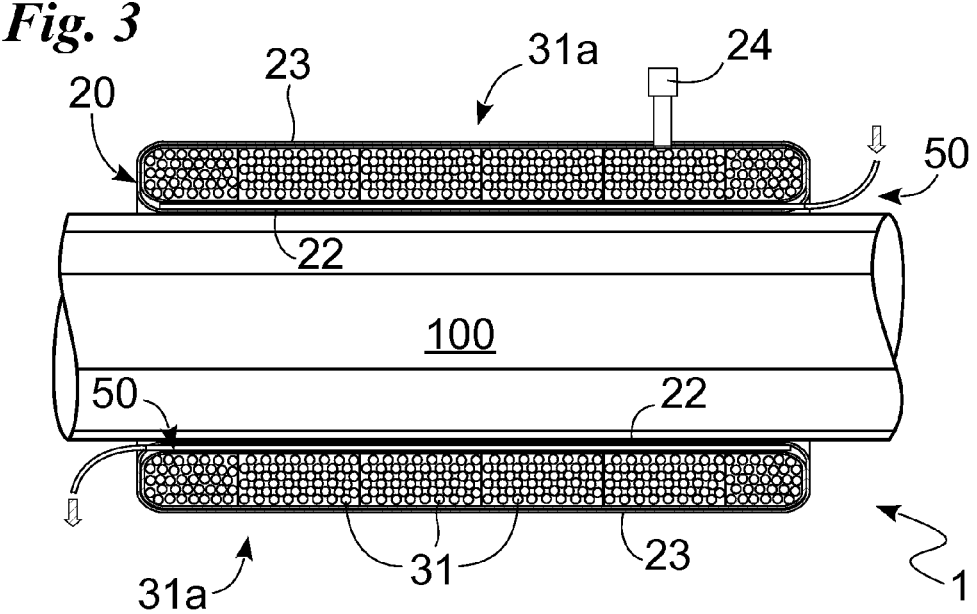
FIG. 3 shows a sagittal section of a variant of the adaptable protective device in the configuration of FIG. 1d.
Figure 2:
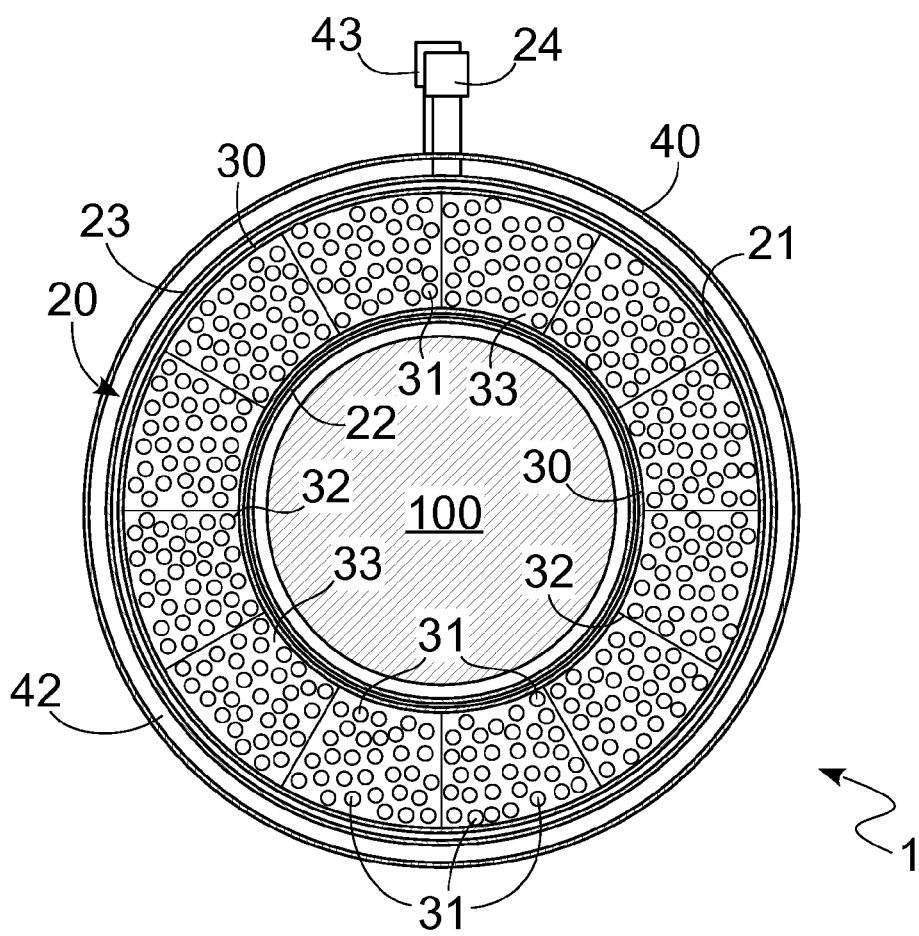

In a last step the valves 24 and 43 can be automatically closed or not, and the closure casing 40 can be moved away from the remainder of the device 1, as illustrated in FIG. 1d.

The invention permits important advantages.

In fact, the device 1 permits to perfectly conform the solid bodies 31a to the shape of a portion of body to protect 100, even if it is not contained within a closed casing.

Such solution works not only in a restricted area, but it is possible to wrap at 360° the portion of body to protect 100.

Such advantage is determined by the uniform and omnidirectional thrust of the atmospheric pressure.

It is then possible to plaster with impeccable precision a portion of a human body and also protect a portion of an object.

Another advantage is due to the fact that it is not necessary to place under vacuum the portion of body 100 if not during the presetting of the device 1.

Another advantage is also due to the heat exchange channel 50 which permits to regulate the temperature of a portion of human body or an object by causing the channel 50 to perfectly abut against the portion of body 100.

The device 1 is finally usable many times, in order to return to the starting configuration (FIG. 1a); in fact, it is sufficient to open the valve 24 permitting the passage of air to the inside of the casing 20.

Due to such advantages, the device 1 can be applied for example: in special packages, such as for transporting organs, unstable liquids (nitroglycerine), weapons, explosives and similar.

Another exemplary embodiment can be a corset for disables, which can stiffen just when necessary.

A further example can be a support for legs for persons having mobility problems.

A further example are armors, for example bulletproof vests, also for women who having breasts risk very serious trauma due to the low ergonomics of the traditional protections, problem obviated through the device 1.

The invention is susceptible of variants all within the inventive concept. All described and claimed items can be substituted with equivalent items and details, materials, shapes and dimensions can be of any kind.

The invention claimed is:

1. An adaptable protective device configured to accommodate a portion of body to protect, comprising:
    a main casing impermeable to passage of fluid, flexible and defining a main volume, said main casing configured to be placed at least partially around said portion of body to protect so that said portion of body to protect is outside said main volume, said main casing defining an inner surface substantially in contact with said portion of body to protect and an outer surface not in contact with said portion of body to protect;
    an inner casing placed inside said main casing, permeable to passage of fluid and flexible;
    a plurality of filler particles housed in said inner casing;
    a first valve suitable to form or interrupt a connection for fluid passage between said main volume and external environment and configured to permit depressurisation of said main volume defining a relaxed configuration in which said filler particles are movable inside said inner casing; and a compressed configuration in which said filler particles are compacted and substantially define at least one solid body;
    a closure casing impermeable to passage of fluid, flexible and comprising sealing means configured to create a fluid seal between said closure casing and said portion of body to protect thereby forming a closed volume impermeable to passage of fluid and including said main casing and said portion of body to protect; and
    a second valve suitable to form or interrupt a connection for fluid passage between said closure volume and external environment and configured to permit depressurisation of said closure volume defining a closed configuration in which said closure casing is depressurised and atmospheric pressure presses, in all directions, said inner casing against said portion of body to protect.

2. The adaptable protective device as claimed in claim 1, comprising a heat exchange channel, inside said main casing and configured to adjust temperature of said portion of body to protect.

3. The adaptable protective device as claimed in the claim 1, wherein said inner casing comprises a plurality of intermediate containers.

4. The adaptable protective device as claimed in the claim 3, wherein said intermediate containers are reciprocally separated by walls.

5. The adaptable protective device as claimed in the claim 1, wherein said inner casing is elastic.

6. The adaptable protective device as claimed in the claim 1, in which said first valve comprises means of connection with the closure casing configured to enable passage of said first valve through the closure casing and its control from the outside.

7. The device of claim 1, wherein the portion of body is a portion of a human or animal.

8. The device of claim 1, wherein the portion of body is a portion of an object.

9. A protection method of a portion of body to protect enacted by means of an adaptable protective device, comprising a main casing impermeable to the passage of fluid, flexible and defining a main volume, an inner casing placed inside said main casing, permeable to passage of fluid and flexible, a plurality of filler particles housed in said inner casing, said method comprising:
 placing said main casing, including said inner casing, around said portion of body to protect, defining an inner surface substantially in contact with said portion of body to protect and an outer surface not in contact with said portion of body to protect,
 placing a closure casing, impermeable to passage of fluid and flexible, around said outer surface of said main casing,
 placing sealing means suitable to create a fluid seal between said closure casing and said portion of body to protect thereby forming a closure volume impermeable to passage of fluid and including said main casing and said portion of body to protect,
 depressurising said closure volume defining a closed configuration in which said closure casing is depressurised and atmospheric pressure presses, in all directions, said inner casing against said portion of body to protect, and
 depressurising said main volume, not before depressurising said closure volume, defining a compressed configuration in which said filler particles are compacted and substantially define at least one solid body.

10. The protection method of a portion of body to protect as claimed in the claim 9, further comprising: after depressurising said main volume, distancing said closure casing from remaining part of the adaptable protective device.

* * * * *